US012383644B2

(12) United States Patent
Kawasaki et al.

(10) Patent No.: US 12,383,644 B2
(45) Date of Patent: Aug. 12, 2025

(54) DECONTAMINATION SYSTEM

(71) Applicant: AIREX CO., LTD., Nagoya (JP)

(72) Inventors: Koji Kawasaki, Nagoya (JP); Gun Sou, Nagoya (JP); Tsukasa Kitano, Nagoya (JP); Zhiqiang Guo, Nagoya (JP); Haruka Futamura, Nagoya (JP); Yukihiro Yazaki, Nagoya (JP); Daisuke Kakuda, Nagoya (JP); Jun Masudome, Nagoya (JP)

(73) Assignee: AIREX CO., LTD., Nagoya (JP)

( * ) Notice: Subject to any disclaimer, the term of this patent is extended or adjusted under 35 U.S.C. 154(b) by 664 days.

(21) Appl. No.: 17/774,770

(22) PCT Filed: Oct. 15, 2020

(86) PCT No.: PCT/JP2020/038956
§ 371 (c)(1),
(2) Date: May 5, 2022

(87) PCT Pub. No.: WO2021/090661
PCT Pub. Date: May 14, 2021

(65) Prior Publication Data

US 2022/0370666 A1 Nov. 24, 2022

(30) Foreign Application Priority Data

Nov. 7, 2019 (JP) ................................ 2019-201886

(51) Int. Cl.
*A61L 2/22* (2006.01)
*B05B 17/00* (2006.01)
*B05B 17/06* (2006.01)

(52) U.S. Cl.
CPC ............ *A61L 2/22* (2013.01); *B05B 17/0646* (2013.01); *B05B 17/0676* (2013.01); *A61L 2209/132* (2013.01)

(58) Field of Classification Search
CPC .. A61L 2/22; A61L 2209/132; A61L 2202/15; A61L 2/025; A61L 2/186;
(Continued)

(56) References Cited

FOREIGN PATENT DOCUMENTS

| | | | |
|---|---|---|---|
| JP | S614543 | A | 1/1986 |
| JP | 2000140729 | A | 5/2000 |

(Continued)

OTHER PUBLICATIONS

WO2015166554(English/Original_Translation) (Year: 2015).*
(Continued)

*Primary Examiner* — James Lin
*Assistant Examiner* — Nebyate Samuel Seged
(74) *Attorney, Agent, or Firm* — Quarles & Brady LLP; Yakov S. Sidorin

(57) ABSTRACT

A decontamination system not requiring large-scale equipment and capable of efficiently using a decontamination liquid. Long pipes can be installed for each of multiple rooms to be decontaminated, a decontamination liquid is not present in supply pipes as a residual dead liquid, and a proper amount of decontamination liquid can essentially be supplied for each room to cause no failure of an ultrasonic vibrator. The system employs a decontamination mist and includes a compressed air generating equipment and a decontamination liquid supplying equipment, and each room is provided with primary and secondary mist generating equipment. The conveyance distance of a primary mist supply pipe connecting the primary and secondary mist generating equipment is longer than that of a decontamination liquid supply pipe connecting the decontamination liquid supplying equipment and the primary mist generating equipment.

16 Claims, 3 Drawing Sheets

(58) Field of Classification Search
CPC .. A61L 2202/25; A61L 2209/134; A61L 9/14; A61L 2/208; A61L 9/015; A61L 2209/211; A61L 2/18; B05B 17/0646; B05B 17/0676; B05B 17/06; B06B 1/0215; B06B 2201/55; B06B 2201/77; B04C 5/14; B04C 9/00
See application file for complete search history.

(56) References Cited

FOREIGN PATENT DOCUMENTS

| | | | | | |
|---|---|---|---|---|---|
| JP | 2005103481 A | * | 4/2005 | | |
| JP | 2006281170 A | | 10/2006 | | |
| JP | 2019062333 A | | 4/2019 | | |
| WO | WO-03024610 A1 | * | 3/2003 | ............... | A61L 2/22 |
| WO | 2004076077 A1 | | 9/2004 | | |
| WO | WO-2015166554 A1 | * | 11/2015 | ............. | A61L 2/208 |
| WO | 2019009376 A1 | | 1/2019 | | |

OTHER PUBLICATIONS

WO 03024610 A1(English/Original_Translation (Year: 2003).*
JP2005103481(English/Original_Translation) (Year: 2005).*
Feinstein, Klostermyer, Warren, Newbould, on behalf of Steris Life Sciences, Vaporous biodecontamination: A matter of efficiency, Jan. 29, 2019, Cleanroom Technology, Feb. 2019 Issue (Year: 2019).*
PCT International Search Report and Written Opinion, PCT/JP2020/038956, Dec. 22, 2020, 10 pages.

* cited by examiner

DECONTAMINATION SYSTEM

CROSS-REFERENCE TO RELATED APPLICATIONS

This application is a U.S. national phase of International Application No. PCT/JP2020/038956 filed on Oct. 15, 2020 and now published as WO 2021/090661, which designates the United States and claims priority from Japanese Patent Application No. 2019-201886 filed on Nov. 7, 2019. The disclosure of each of these patent applications is incorporated by reference herein.

TECHNICAL FIELD

The present invention relates to a decontamination system configured to decontaminate an indoor working area such as not only an isolator, a RABS, and a clean room, but also a passing room and a pass box associated therewith by generating a mist for decontamination in the working area.

BACKGROUND ART

In manufacturing settings for pharmaceutical or food products or in the clinical environment such as operating rooms, the indoor working area must inevitably be kept sterile. Particularly in cases where clean rooms as a working chamber for manufacturing pharmaceutical products are decontaminated, advanced decontamination validation needs to be accomplished in accordance with Good Manufacturing Practice (GMP).

In recent years, hydrogen peroxide gas has widely been used to decontaminate a working chamber requiring sterile environment (hereinafter referred to as a "room to be decontaminated"). Advantageously, hydrogen peroxide gas has a strong sterilization effect, and is inexpensively available and effectively utilized as an environmentally-friendly decontamination gas that is ultimately resolved into oxygen and water. Nevertheless, hydrogen peroxide gas has conventionally been utilized to decontaminate individual rooms to be decontaminated, for example, small spaces such as a clean room, an isolator, and a glove box. Unfortunately, however, use of hydrogen peroxide gas for decontaminating a single large-space or multiple rooms to be decontaminated essentially involved stable supply of a predetermined concentration of hydrogen peroxide gas in large quantities.

Accordingly, supply of a large amount of hydrogen peroxide gas from a decontamination gas generation device to a room to be decontaminated inevitably involved large-scale works of large-diameter, corrosion-resistant ducts and heater equipment for keeping warm such ducts.

In manufacturing settings for pharmaceutical products, in particular, two or more rooms to be decontaminated may often be provided, and must be decontaminated simultaneously. In this case, each room to be decontaminated should not be provided with a decontamination liquid supply unit and a decontamination gas generation device, because each decontamination gas generation device needs duct works, which makes the entire system inefficient. In order to avoid such an inefficient system, long main ducts are installed from one decontamination gas generation device to multiple rooms to be decontaminated, each room to be decontaminated being further provided with branch ducts for simultaneous decontamination. In this case, it is hard to properly determine the amount of a hydrogen peroxide gas supplied because branched parts of a duct are prone to condensation and the distance between the decontamination gas generation device and each room to be decontaminated varies.

Meanwhile, the following patent document 1 describes that the decontamination effect by hydrogen peroxide is provided by a condensed film of a hydrogen peroxide solution that condenses on the surface of an object to be decontaminated. Inventors of the present invention found that a fine mist of hydrogen peroxide solution (hereinafter referred to as a "hydrogen peroxide mist"), instead of a hydrogen peroxide gas, is supplied to a room to be decontaminated to achieve efficient decontamination using the least possible amount of decontamination agent, and suggests the technique as described in the following patent document 2.

It is thus contemplated that a hydrogen peroxide mist is supplied to one or more rooms to be decontaminated for precise and efficient decontamination. Even in this case, however, it is not an effective approach to provide a decontamination liquid supply unit and a mist generation device (e.g., ultrasonic atomizer) for each room to be decontaminated to control the amount of decontamination liquid supplied for each room and decontamination conditions. A possible solution is to arrange long supply pipes from one decontamination liquid supply unit to multiple rooms to be decontaminated to supply a decontamination liquid to a mist generation device provided from the supply pipes to each room to be decontaminated (it is possible to install a compact and sophisticated ultrasonic atomizer in each room) and generate a hydrogen peroxide mist for each room to be decontaminated for simultaneous decontamination.

CITATION LIST

Patent Literature

Patent Document 1: JP-A-61-004543
Patent Document 2: JP-A-2019-062333

SUMMARY OF INVENTION

Technical Problem

In this case, if a sufficient amount of decontamination liquid is supplied to an ultrasonic atomizer in each room to be decontaminated, a decontamination liquid is inefficiently present in long supply pipes as a residual dead liquid, and it is unfortunately hard to control the amount of a decontamination liquid supplied for each room. Meanwhile, when the least possible amount of decontamination liquid is supplied to an ultrasonic atomizer to efficiently use the decontamination liquid, possible insufficient supply of the decontamination liquid and its subsequent shortage thereof lead directly to failure of an ultrasonic vibrator, which is the core of the ultrasonic atomizer.

Thus, the present invention was made in view of the situation to solve the problems, and has an object to provide a decontamination system capable of efficiently using a decontamination liquid because large-scale equipment such as large-diameter ducts and anti-condensation heaters is not required, long pipes can be installed for each of a plurality of rooms to be decontaminated, a decontamination liquid is not present in supply pipes as a residual dead liquid, and a proper amount of decontamination liquid can essentially be supplied for each room to cause no failure of an ultrasonic vibrator.

Solution to Problem

To solve the aforementioned problem, inventors of the present invention have carried out an extended investigation to find that a primary mist obtained by mixing a hydrogen peroxide solution with compressed air using a small-diameter supply pipe is supplied to each room to be decontaminated through the supply pipe and the primary mist is subjected to gas-liquid separation adjacent to each room to be decontaminated or indoor to convert the separated hydrogen peroxide solution into a fine secondary mist using an ultrasonic atomizer. Based on that technique, the present invention was accomplished.

Specifically, a decontamination system according to the present invention is, according to description in claim 1, a decontamination system (100) for decontaminating the inside of each of one or more rooms to be decontaminated (R1 to Rn) using a mist for decontamination, the system including a compressed air generation means (10) for generating compressed air and a decontamination liquid supply means (20) for supplying a decontamination liquid that constitutes a mist for decontamination, and primary mist generation means (E1 to En) for generating a primary mist by mixing the compressed air and the decontamination liquid for each room to be decontaminated, secondary mist generation means (M1 to Mn, Mx, My) for converting a decontamination liquid subjected to gas-liquid separation from the primary mist into a fine secondary mist, air supply pipes (AL1 to ALn) for communicating from the compressed air generation means to the primary mist generation means, decontamination liquid supply pipes (LL1 to LLn) for communicating from the decontamination liquid supply means to the primary mist generation means, and primary mist supply pipes (ML1 to MLn, MLx, MLy) for communicating from the primary mist generation means to the secondary mist generation means, characterized in that the secondary mist generation means include primary mist receiving containers (R1 to Rn, Rx, Ry) and ultrasonic atomizers (A1 to An, Ax, Ay), the primary mist receiving containers each include an air vent (MRx2, MRy2) for discharging the air subjected to gas-liquid separation from the primary mist supplied through the primary mist supply pipes to the outside, and the ultrasonic atomizers each include a piezoelectric vibrator (Ax2, Ay2) and a perforated vibration plate (Ax1, Ay1) provided with a plurality of micropores atomizing the decontamination liquid subjected to gas-liquid separation by vibration of the piezoelectric vibrator, the micropores passing through the perforated vibration plate between the front surface and the back surface thereof.

Moreover, the present invention is, according to description in claim 2, the decontamination system according to claim 1, characterized in that the compressed air generation means, the decontamination liquid supply means, and each of the primary mist generation means are arranged so as to be separate from each of the rooms to be decontaminated through the primary mist supply pipes, each of the secondary mist generation means is arranged adjacent to each corresponding room to be decontaminated or indoor through each of the primary mist supply pipes, whereby the conveyance distance of each of the primary mist supply pipes to each room to be decontaminated is longer than the conveyance distance of each of the decontamination liquid supply pipes corresponding to the room to be decontaminated.

Furthermore, the present invention is, according to description in claim 3, the decontamination system according to claim 1 or 2, characterized in that the ultrasonic atomizer is disposed such that the front surface of the perforated vibration plate faces the inside of the room to be decontaminated and the rear surface faces the inside of the primary mist receiving container, and the primary mist supplied to the primary mist receiving container is ejected from the primary mist supply pipe onto the rear surface of the perforated vibration plate to be subjected to gas-liquid separation, and is atomized when the separated decontamination liquid moves from the rear surface to the front surface of the perforated vibration plate to be discharged from the front surface into the inside of the room to be decontaminated.

Furthermore, the present invention is, according to description in claim 4, the decontamination system according to claim 1 or 2, characterized in that the ultrasonic atomizer is disposed such that the front surface of the perforated vibration plate faces the inside of the room to be decontaminated and the rear surface faces a liquid pool provided at an internal lower end portion of the primary mist receiving container, and the primary mist supplied to the primary mist receiving container is discharged from the primary mist supply pipe into the inside of the primary mist receiving container to be subjected to gas-liquid separation, and is atomized after the separated decontamination liquid is collected at the liquid pool of the primary mist receiving container and moves from the rear surface to the front surface of the perforated vibration plate to be discharged from the front surface into the inside of the room to be decontaminated.

Furthermore, the present invention is, according to description in claim 5, the decontamination system according to claim 4, characterized in that the primary mist receiving container is spindle-shaped or semi-spindle-shaped with a focusing lower end portion, or has a spindle-shaped cross section or a semi-spindle-shaped cross section with a focusing lower end portion, and the supplied primary mist is subjected to gas-liquid separation, the separated decontamination liquid is collected at the liquid pool provided at the lower end portion and the separated air is discharged from the air vent provided at an upper end portion into the outside.

Furthermore, the present invention is, according to description in claim 6, the decontamination system according to claim 4, characterized in that the primary mist receiving container subjects the primary mist supplied by a cyclone mechanism to gas-liquid separation, the separated decontamination liquid is collected at the liquid pool provided at the lower end portion and the separated air is discharged from the air vent provided at the upper end portion into the outside.

Moreover, the present invention is, according to description in claim 7, the decontamination system according to any one of claims 1 to 6, including mist dispersion/diffusion means (V1 to Vn) for dispersing and diffusing the secondary mist, characterized in that the mist dispersion/diffusion means each include an ultrasonic vibration plate disposed on an internal wall surface of the room to be decontaminated, the ultrasonic vibration plate is subjected to ultrasonic vibration to generate sound flows from a plate surface by an ultrasound, and the secondary mist discharged from the secondary mist generation means is pressed by acoustic radiation pressure in stationary operation, intermittent operation or stronger/weaker operation to disperse and diffuse the secondary mist.

Moreover, the present invention is, according to description in claim 8, the decontamination system according to claim 7, characterized in that the secondary mist supplied to the inside of the decontamination region is further refined by ultrasonic vibration generated from the ultrasonic vibration plate.

Moreover, the present invention is, according to description in claim 9, the decontamination system according to any one of claims 1 to 6, including mist dispersion/diffusion means (W1 to Wn) for dispersing and diffusing secondary mist, characterized in that the mist diffusion means each include an axial fan disposed adjacent to the secondary mist generation means, the secondary mist discharged from the secondary mist generation means by the axial fan is pressed by air flow in stationary operation, intermittent operation or stronger/weaker operation to disperse and diffuse the secondary mist.

Advantageous Effects of Invention

According to the above configuration, a decontamination liquid, which is the source of a mist for decontamination, is mixed with compressed air generated in a compressed air generation means by a primary mist generation means to be converted into a primary mist. The primary mist is supplied to a secondary mist generation means through a primary mist supply pipe to be converted into a fine hydrogen peroxide mist, which is a secondary mist. Herein, a primary mist is a high-density, mixed mist of compressed air and decontamination liquid with a high conveyance, speed, and a primary mist supply pipe used may be a small-diameter pipe. Therefore, even in cases where multiple rooms to be decontaminated are provided and the distance of a primary mist supply pipe installed to each room to be decontaminated varies, each room to be decontaminated is provided with a proper pipe distance, and as required, the distance can be longer. Accordingly, large-scale equipment such as large-diameter ducts is not required.

Also, a hydrogen peroxide solution in a primary mist is present as a liquid, thereby requiring no warming of primary mist supply pipes to prevent condensation. Therefore, even in cases where multiple rooms to be decontaminated are provided and long supply pipes are installed for each room to be decontaminated, large-scale equipment such as anti-condensation heaters is not required.

According to the above configuration, while a plurality of rooms to be decontaminated share a compressed air generation means and a decontamination liquid supply means, each of these rooms to be decontaminated is provided with a primary mist generation means, a secondary mist generation means and a primary mist supply pipe connecting these two means (hereinafter referred to as “decontamination unit”). Accordingly, the compressed air generation means, the decontamination liquid supply means and each primary mist generation means can be arranged so as to be separate from each of the rooms to be decontaminated. Meanwhile, each secondary mist generation means is arranged adjacent to each corresponding room to be decontaminated or indoor. Accordingly, each room to be decontaminated is provided with a separate decontamination unit, with the shorter conveyance distance of a decontamination liquid supply pipe and the longer conveyance distance of a gas/liquid mixture supply pipe. Accordingly, long pipes can be installed for each of a plurality of rooms to be decontaminated.

Thus, setting a shorter conveyance distance of a decontamination liquid supply pipe can accurately determine the amount of a decontamination liquid supplied to a primary mist generation means. Accordingly, the amount of a decontamination liquid supplied to a secondary mist generation means for each room to be decontaminated can accurately be determined, and the amount of a secondary mist discharged into the room to be decontaminated is clearly determined. Meanwhile, the hydrogen peroxide solution in the primary mist, which is present as a liquid, is not condensed, thereby conveying a decontamination liquid over a long distance and accurately by elongating the conveyance distance of the primary mist supply pipe. Moreover, complete conveyance of the hydrogen peroxide solution in the pipe by compressed air allows no residual dead liquid to stay in the pipe. Also, an accurate determination of the amount of a hydrogen peroxide solution supplied to the secondary mist generation means as a primary mist causes no shortage of hydrogen peroxide solution, resulting in no failure of an ultrasonic vibrator of the secondary mist generation means. Accordingly, the decontamination liquid can efficiently be utilized.

According to the above configuration, an ultrasonic atomizer may be disposed such that the front surface of a perforated vibration plate faces the inside of the room to be decontaminated and the rear surface faces the inside of a primary mist receiving container. The primary mist supplied to the primary mist receiving container in this state is directly ejected onto the rear surface of the perforated vibration plate from the primary mist supply pipe to be subjected to gas-liquid separation on the rear surface of the perforated vibration plate. The separated decontamination liquid is atomized when it moves from the rear surface to the front surface of the perforated vibration plate to be discharged from the front surface into the inside of the room to be decontaminated.

According to the above configuration, the ultrasonic atomizer may be disposed such that the front surface of the perforated vibration plate faces the inside of the room to be decontaminated and the rear surface faces a liquid pool provided at an internal lower end portion of the primary mist receiving container. The primary mist supplied to the primary mist receiving container in this state is discharged into the inside of the primary mist receiving container to be subjected to gas-liquid separation. The separated decontamination liquid is collected at the liquid pool of the primary mist receiving container and atomized when it moves from the rear surface to the front surface of the perforated vibration plate to be discharged from the front surface into the inside of the room to be decontaminated.

According to the above configuration, the primary mist receiving container may be spindle-shaped or semi-spindle-shaped with a focusing lower end portion. In addition, the primary mist receiving container may have a spindle-shaped cross section or a semi-spindle-shaped cross section with a focusing lower end portion. Accordingly, the decontamination liquid subjected to gas-liquid separation from the supplied primary mist is collected in a liquid pool provided at the lower end portion of the primary mist receiving container. Meanwhile, the separated air is discharged from an air vent provided at the upper end portion of the primary mist receiving container into the outside.

According to the above configuration, the primary mist receiving container may include a cyclone mechanism. Accordingly, the decontamination liquid subjected to gas-liquid separation from the supplied primary mist is collected in the liquid pool provided at the lower end portion of the primary mist receiving container. Meanwhile, the separated air is discharged from an air vent provided at the upper end portion of the primary mist receiving container into the outside.

According to the above configuration, the decontamination system may include mist dispersion/diffusion means for dispersing and diffusing a secondary mist. The mist dispersion/diffusion means each include an ultrasonic vibration plate disposed on an internal wall surface of the room to be decontaminated, and the ultrasonic vibration plate is subjected to ultrasonic vibration to generate sound flows from a plate surface by an ultrasound. Accordingly, the secondary mist discharged from the secondary mist generation means is pressed by acoustic radiation pressure in stationary operation, intermittent operation or stronger/weaker operation to disperse and diffuse the secondary mist. According to the above configuration, the secondary mist supplied to the inside of the room to be decontaminated is further refined by ultrasonic vibration generated from the ultrasonic vibration plate.

According to the above configuration, the decontamination system may include mist diffusion means for dispersing and diffusing a secondary mist. The mist diffusion means each include an axial fan disposed adjacent to the secondary mist generation means, and the secondary mist discharged from the secondary mist generation means by the axial fan is pressed by air flow in stationary operation, intermittent operation or stronger/weaker operation to disperse and diffuse the secondary mist.

Thus, the present invention can provide a decontamination system capable of efficiently using a decontamination liquid because large-scale equipment such as large-diameter ducts and anti-condensation heaters is not required, long pipes can be installed for each of a plurality of rooms to be decontaminated, a decontamination liquid is not present in supply pipes as a residual dead liquid, and a proper amount of decontamination liquid can essentially be supplied for each room to cause no failure of an ultrasonic vibrator.

DESCRIPTION OF EMBODIMENTS

The decontamination system according to the present invention will be described with reference to each of the embodiments. The present invention is not restricted to each of the following embodiments.

First Embodiment

Figure 1:
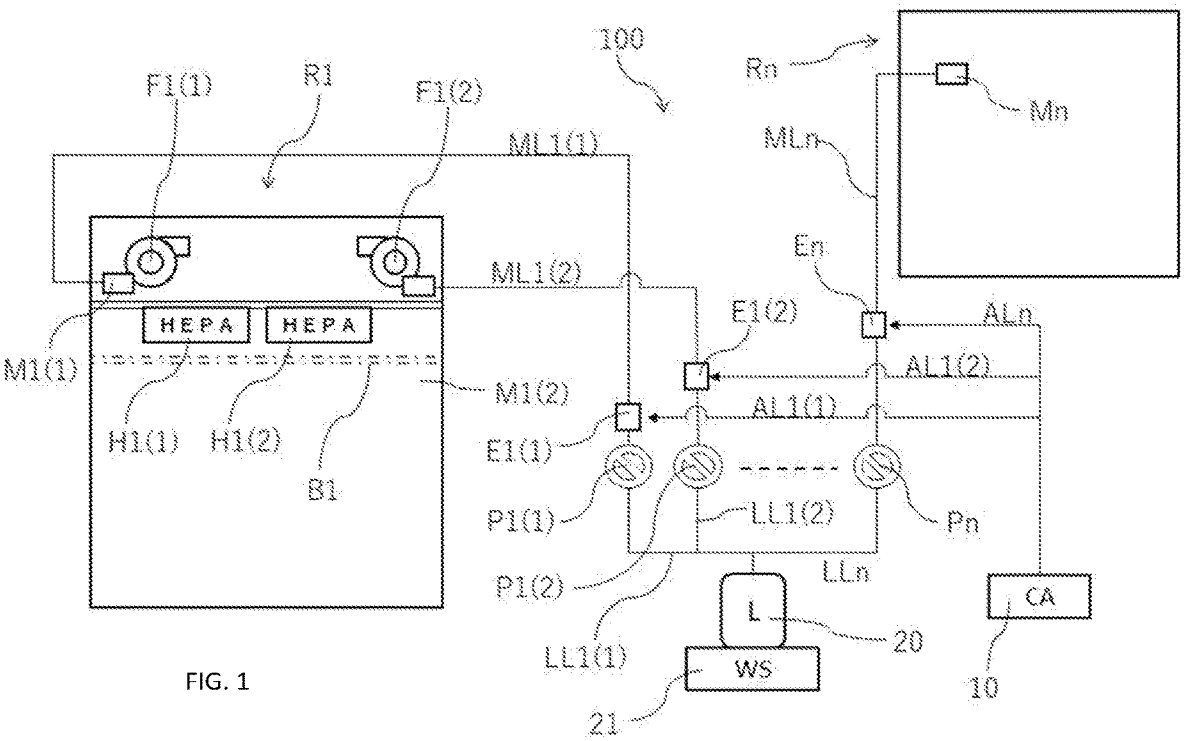
FIG. 1 is a schematic block diagram illustrating a decontamination system according to a first embodiment of the present invention.

A first embodiment of the decontamination system according to the present invention will be described with reference to the drawings. FIG. 1 is a schematic block diagram illustrating a decontamination system 100 according to the first embodiment. In this first embodiment, as illustrated in FIG. 1, an isolator is composed of "n" rooms to be decontaminated (n is a positive integer), each denoted by R1 to Rn and having different capacities. Each room to be decontaminated, having a separate space, is provided at an upper portion therein with circulating fans F1 to Fn, HEPA filters H1 to Hn, and straightening plates B1 to Bn.

In this first embodiment, an isolator is composed of "n" rooms to be decontaminated, but the structure of an isolator is not restricted thereto, and the isolator may be RABS, a clean room, a passing room, a pass box, or a combination thereof. There may also be one or more rooms to be decontaminated.

In FIG. 1, the decontamination system 100 includes an air compressor 10 and a hydrogen peroxide solution tank 20, which are shared by rooms to be decontaminated R1 to Rn. The rooms to be decontaminated R1 to Rn include ejectors E1 to En for generating a primary mist and hydrogen peroxide mist generation devices M1 to Mn, respectively. The hydrogen peroxide mist generation devices M1 to Mn act as a secondary mist generation means. In FIG. 1, the room to be decontaminated R1 has 2 ejectors E1(1), E1(2), and 2 hydrogen peroxide mist generation devices M1(1), M1(2). Meanwhile, the room to be decontaminated Rn has one ejector En and one hydrogen peroxide mist generation device Mn. This different configuration depends on the internal capacity of each room to be decontaminated.

The air compressor 10 acts as a compressed air generation means for generating compressed air, which is a carrier gas for conveying a hydrogen peroxide solution. The air compressor 10 is arranged so as to be separate from each of the rooms to be decontaminated R1 to Rn.

The hydrogen peroxide solution tank 20 acts as a decontamination liquid supply means for storing a hydrogen peroxide solution, which is the source of a hydrogen peroxide mist as a mist for decontamination. The hydrogen peroxide solution tank 20 is disposed adjacent to the air compressor 10 so as to be separate from each of the rooms to be decontaminated R1 to Rn. Herein, the concentration of the hydrogen peroxide solution stored in the hydrogen peroxide solution tank 20 is not particularly restricted, and in general, it is preferably 30 to 35% by weight in view of hazardous materials in use. Also, the hydrogen peroxide solution tank 20 includes a weighing device 21 for detecting the remaining amount of a hydrogen peroxide solution therein and a controller (not shown) for controlling the remaining amount.

The ejectors E1 to En act as a primary mist generation means for generating a primary mist by mixing a hydrogen peroxide solution with compressed air. The ejectors E1 to En are disposed adjacent to the air compressor 10 and the hydrogen peroxide solution tank 20 so as to be separate from each of the rooms to be decontaminated R1 to Rn.

The hydrogen peroxide mist generation devices M1 to Mn are configured by mist receiving containers MR1 to MRn and ultrasonic atomizers A1 to An (both not shown in FIG. 1, but the structure is later-described). The mist receiving containers MR1 to MRn act as a primary mist receiving container for receiving a primary mist containing a hydrogen peroxide solution conveyed from the ejectors E1 to En and subjecting the mist to gas-liquid separation. Also, the mist receiving containers MR1 to MRn supply the separated hydrogen peroxide solution to the ultrasonic atomizers A1 to An and discharge the separated air into the outside. The structure of the mist receiving containers MR1 to MRn is described later.

In FIG. 1 illustrating this first embodiment, the hydrogen peroxide mist generation devices M1 to Mn are disposed at an upper portion of HEPA filters H1 to Hn (adjacent to circulating fans F1 to Fn). In this case, the generated mist is diffused by the circulating fans F1 to Fn in operation. In addition, the position of the hydrogen peroxide mist generation devices M1 to Mn is not particularly restricted thereto, and it may be disposed inside or outside a side wall. Even in cases where the hydrogen peroxide mist generation devices M1 to Mn are disposed outside the rooms to be decontaminated R1 to Rn, a discharge port for the hydrogen peroxide mist is open inside the rooms to be decontaminated R1 to Rn.

The ultrasonic atomizers A1 to An receive a hydrogen peroxide solution subjected to gas-liquid separation from the mist receiving containers MR1 to MRn, generate a fine secondary mist, and discharge the same into the inside of the rooms to be decontaminated R1 to Rn. The ultrasonic atomizers A1 to An constitute the hydrogen peroxide mist generation devices M1 to Mn acting as the secondary mist generation means, together with the mist receiving containers MR1 to MRn. The structure of the ultrasonic atomizers A1 to An is described later.

The biggest room to be decontaminated R1, as described above, is provided with 2 decontamination units (2 ejectors E1(1), E1(2), 2 hydrogen peroxide mist generation devices M1(1), M1(2), and 2 primary mist supply pipes ML1(1), ML1(2)). This is because that the decontamination efficiency can be higher by discharging a hydrogen peroxide mist from 2 sets of separate decontamination units into the large-capacity room to be decontaminated R1 than by supplying a hydrogen peroxide mist in large quantities to the room to be decontaminated R1 only from a set of decontamination unit. Also, 2 or more decontamination units may be provided for one room, depending on the capacity of the room to be decontaminated. Accordingly, even in cases where a plurality of decontamination units is provided for one room, a primary mist supply pipe can be small in diameter, thereby saying equipment costs.

In FIG. 1, the decontamination system 100 includes air supply pipes AL1 to ALn communicating the air compressor 10 and the ejectors E1 to En, decontamination liquid supply pipes LL1 to LLn communicating the hydrogen peroxide solution tank 20 and the ejectors E1 to En, and primary mist supply pipes ML1 to MLn communicating the ejectors E1 to En and the mist receiving containers MR1 to MRn.

The air supply pipes AL1 to ALn communicate an ejection port of the air compressor 10 and a driving flow path (not shown) of each of the ejectors E1 to En. Conduit lines of the air supply pipes AL1 to ALn are each provided with an on-off valve (not shown) controlling the supply of compressed air. Herein, the material and diameter of the air supply pipes AL1 to ALn are not particularly restricted, and in general, such a pipe is preferably a stainless pipe having an internal diameter of 1 to 10 mm. A conduit line between the air compressor 10 and each of the air supply pipes AL1 to ALn may be provided with an air dryer, an air regulator, an auto-drain, an oil mist separator, and other filter (each not shown in FIG. 1).

Each of the decontamination liquid supply pipes LL1 to LLn communicates a supply port of the hydrogen peroxide solution tank 20 and a suction flow path (not shown) of each of the ejectors E1 to En. Conduit lines of the decontamination liquid supply pipes LL1 to LLn are provided with tube pumps P1 to Pn controlling the supply of a hydrogen peroxide solution, respectively. Herein, the material and diameter of the decontamination liquid supply pipes LL1 to LLn are not particularly restricted so long as they can serve for a hydrogen peroxide solution, and in general, such a pipe is preferably a stainless pipe having an internal diameter of 1 to 10 mm.

The primary mist supply pipes ML1 to MLn each communicate an ejection flow path of each of the ejectors E1 to En and the mist receiving containers MR1 to MRn that constitute the ultrasonic atomizers A1 to An. The primary mist supply pipes ML1 to MLn are installed over a long distance from the vicinity of the air compressor 10 and the hydrogen peroxide solution tank 20 to the hydrogen peroxide mist generation devices M1 to Mn disposed inside an upper wall of each of the rooms to be decontaminated. R1 to Rn, Herein, the material and diameter of the primary mist supply pipes ML1 to MLn may preferably be determined so long as it is possible to convey a required amount of hydrogen peroxide mist over a long distance per unit time, and in general, such a pipe is preferably a stainless pipe having an internal diameter of 1 to 10 mm.

Thus, a hydrogen peroxide mist can separately be discharged into each room to be decontaminated to accurately decontaminate each room by installing the air supply pipes AL1 to ALn, the decontamination liquid supply pipes LL1 to LLn and the primary mist supply pipes ML1 to MLn for the rooms to be decontaminated R1 to Rn.

As shown in FIG. 1, the conveyance distance of each of the primary mist supply pipes ML1 to MLn is longer than the conveyance distance of each of the air supply pipes AL1 to ALn or the conveyance distance of each of the decontamination liquid supply pipes LL1 to LLn. The conveyance distance of the primary mist by each of the primary mist supply pipes ML1 to MLn is not particularly restricted, and normally is 3 to 100 m or so. Meanwhile, the conveyance distance of each of the air supply pipes AL1 to ALn or the conveyance distance of each of the decontamination liquid supply pipes LL1 to LLn can be shortened.

In this first embodiment, the primary mist is a high-density gas/liquid mixture of compressed air and hydrogen peroxide solution with a high conveyance speed, and the primary mist supply pipes ML1 to MLn may each be a small-diameter pipe. Therefore, the rooms to be decontaminated can be provided with long primary mist supply pipes ML1 to MLn. Accordingly, large-scale equipment such as large-diameter ducts is not required.

Also, a hydrogen peroxide solution in the primary mist is present as a liquid, thereby requiring no warming of the primary mist supply pipes ML1 to MLn to prevent condensation. Therefore, even in cases where a long pipe is installed for each room to be decontaminated, large-scale equipment such as anti-condensation heaters is not required.

Thus, selling a shorter conveyance distance of each of the decontamination liquid supply pipes LL1 to LLn can accurately determine the amount of a hydrogen peroxide solution supplied to each of the ejectors E1 to En. Accordingly, the amount of the hydrogen peroxide solution supplied to the mist receiving containers MR1 to MRn for each room to be decontaminated can accurately be determined, and the amount of a hydrogen peroxide mist discharged into the room to be decontaminated is clearly determined. Meanwhile, the hydrogen peroxide solution in the primary mist, which is present as a liquid, is not condensed, thereby conveying a hydrogen peroxide solution over a long distance and accurately by elongating the conveyance distance of the primary mist supply pipes ML1 to MLn. Moreover, complete conveyance of the hydrogen peroxide solution in the primary mist supply pipes ML1 to MLn by compressed air allows no residual dead liquid to stay in the pipe.

Subsequently, a method for decontaminating rooms to be decontaminated R1 to Rn, using a decontamination system 100 of this first embodiment, will be described.

In this first embodiment, 4 rooms to be decontaminated R1 to Rn are decontaminated for the same duration for generating a mist for decontamination. The amount of a hydrogen peroxide mist to be discharged per unit time is determined for rooms to be decontaminated, each having a different capacity. The amount of a hydrogen peroxide solution, which is supplied from the hydrogen peroxide solution tank 20 through the decontamination liquid supply pipes LL1 to LLn for the ejectors E1 to En corresponding to the rooms to be decontaminated, is determined from the amounts of the mist for decontamination discharged. In addition, predetermined conditions are preferably set for each room before decontamination, using temperature regulation equipment and humidity regulation equipment.

Subsequently, a decontamination operation is started. First, an on-off valve (not shown) of each of the air supply pipes AL1 to ALn is opened to supply compressed air from the air compressor 10 to a driving flow path of each of the ejectors E1 to En through each of the air supply pipes AL1 to ALn. Herein, the compressed air supplied to each of the ejectors E1 to En is not particularly restricted, and the ejection pressure is preferably 0.05 MPa or more, and the air flow amount is preferably 0.5 to 20 NL/min. The air flow amount may be determined according to the concentration and amount of a hydrogen peroxide solution supplied to each room to be decontaminated and the distance to each room to be decontaminated.

Subsequently, the tube pumps P1 to Pn of the decontamination liquid supply pipes LL1 to LLn are operated to supply a hydrogen peroxide solution from the hydrogen peroxide solution tank 20 to a suction flow path of each of the ejectors E1 to En through each of the decontamination liquid supply pipes LL1 to LLn. Also, the amount of the hydrogen peroxide solution supplied corresponds to that determined as above for each of the ejectors E1 to En. Herein, the concentration of the hydrogen peroxide solution supplied to each of the ejectors E1 to En is not particularly restricted, and in general, it may be 30 to 35% by weight as currently used, or may be used by concentrating or diluting the solution. The flow amount of the hydrogen peroxide solutions supplied to each of the ejectors E1 to En may be 0.5 to 10 g/min.

With the amounts of a hydrogen peroxide solution and compressed air being in the above ranges, a primary mist obtained by mixing a hydrogen peroxide solution through each of the primary mist supply pipes ML1 to MLn can be conveyed even over a long distance.

By the above operation, the ejectors E1 to En convert the hydrogen peroxide solution and compressed air into a primary mist, which is supplied to each of the mist receiving containers MR1 to MRn that constitute the hydrogen peroxide mist generation devices 111 to Mn through each of the primary mist supply pipes ML1 to MLn from the ejection flow path of each of the ejectors E1 to En.

In the mist receiving containers MR1 to MRn, the primary mist is subjected to gas-liquid separation to generate a hydrogen peroxide solution and air. The hydrogen peroxide subjected to gas-liquid separation in each of the mist receiving containers MR1 to MRn is supplied to the ultrasonic atomizers A1 to An having a discharge port in the rooms to be decontaminated R1 to Rn from the mist receiving containers MR1 to MRn. At this stage, an ultrasonic vibrator (later-described) of each of the ultrasonic atomizers A1 to An starts operation. Accordingly, a fine hydrogen peroxide mist generated in each of the ultrasonic atomizers A1 to An is discharged into each room to be decontaminated to uniformly decontaminate each room to be decontaminated.

In the present invention, "mist" is broadly interpreted as the state of a liquid droplet of a decontamination agent refined and floating in the air, the state of a gas and a liquid agent of a decontamination agent in mixture, the state of the decontamination agent to repeat the change in phase between condensation and evaporation of a gas and a droplet, and the like, in terms of particle size as well, the mist is also broadly interpreted to include mists, fogs, and liquid droplets, which can be subclassified.

Accordingly, the mist according to the present invention is categorized into a "mist" the size may be defined as 10 μm or less) or a "fog" (the size may be defined as 5 μm or less), and a mist having a larger particle size. In the present invention, the ultrasonic atomizers A1 to An convert even a mist, a fog and a liquid droplet sized 3 to 10 μm or more into equalized ultrafine particles 5 μm or less or 3 μm or less to provide high-level decontamination effects.

Accordingly, a hydrogen peroxide mist is discharged for a predetermined period of time. After the predetermined period of time has elapsed, the tube pumps P1 to Pn of the decontamination liquid supply pipes LL1 to LLn are stopped to stop supply of a hydrogen peroxide solution. At this stage, compressed air is being supplied to each of the ejectors E1 to En through each of the air supply pipes AL1 to ALn, and a residual hydrogen peroxide solution in each of the primary mist supply pipes MIA to MLn is all sent to each of the mist receiving containers MR1 to MRn. Accordingly, a predetermined amount of hydrogen peroxide mist is accurately discharged into the rooms to be decontaminated R1 to Rn. When the hydrogen peroxide solution supplied to the ultrasonic atomizers A1 to An is all converted into a mist, an ultrasonic vibrator (later-described) of each of the ultrasonic atomizers A1 to An stops operation.

Subsequently, on-off valves 11*a* to 15*a* of the air supply pipes AL1 to ALn are closed to stop supply of compressed air. Thereafter, the hydrogen peroxide mist inside the room is discharged to aerate the inside of the room and complete the decontamination operation. Each of the above operations is preferably automatically controlled using a micro-computer.

Figure 5A:
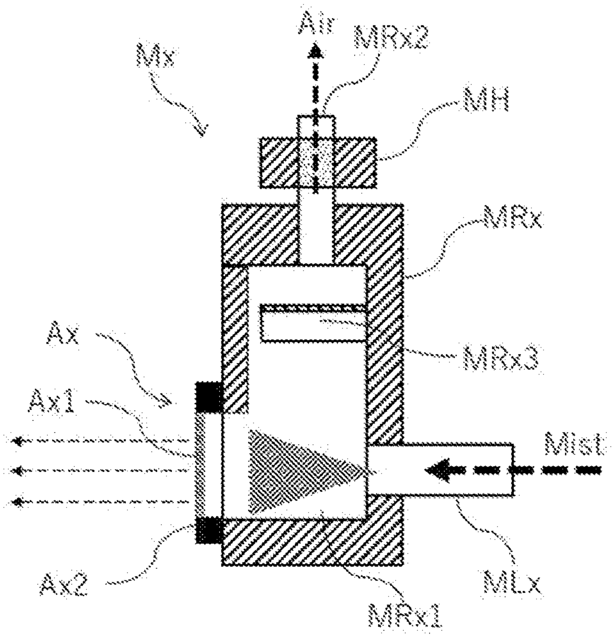
FIG. 5A is a front view illustrating an exemplary secondary mist generation means used in the decontamination system of the present invention seen from the room to be decontaminated side.
Figure 5B:
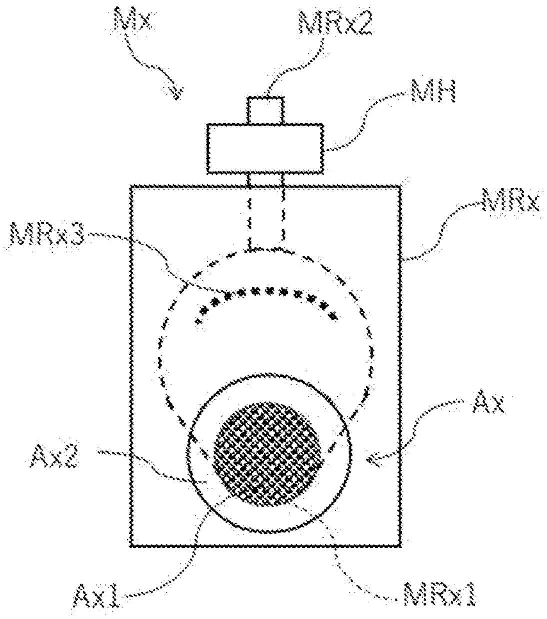
FIG. 5B is a schematic side cross-sectional view illustrating the same.

Herein, one exemplary secondary mist generation means used in this first embodiment will be described. FIGS. 5A, 5B illustrate one exemplary secondary mist generation means. FIG. 5A is a front view of the secondary mist generation means seen from the room to be decontaminated side, and FIG. 5B is a schematic side cross-sectional view thereof. In these figures, a hydrogen peroxide mist generation device Mx as a secondary mist generation means is shown composed of a mist receiving container MRx and an ultrasonic atomizer Ax.

The mist receiving container MRx constitutes a space with a front internal portion having a semi-spindle-shaped cross section, and an ultrasonic atomizer Ax is attached to a front lower end portion with a semi-spindle-shaped focusing width. A lower end portion of the internal space is provided with a focusing width to serve as a liquid pool MRx1 for a small amount of decontamination liquid subjected to gas-liquid separation. Also, an end of a primary mist supply pipe MLx communicates with a rear lower end portion of the mist receiving container MRx (at a position opposite the ultrasonic atomizer Ax) toward the inside of the mist receiving container MRx. An air vent MRx2 opens at the upper end portion inside a rear surface of the mist receiving container MRx. Also, a path of the air vent MRx2 may be provided with a filter MH resolving hydrogen peroxide. Also, a baffle plate MRx3 is provided between an end of the primary mist supply pipe MLx in the center inside the mist receiving container MRx and the air vent MRx2.

The ultrasonic atomizer Ax is composed of a substantially annular disk-shaped perforated vibration plate Ax1 provided with a plurality of micropores (not shown) atomizing the decontamination liquid (hydrogen peroxide solution) subjected to gas-liquid separation, the micropores passing through the perforated vibration plate between the front surface and the back surface thereof, a piezoelectric vibrator Ax2 formed of a substantially annular disk in which the perforated vibration plate Ax1 is subjected to film vibration, and a controller (not shown) controlling the vibration of the piezoelectric vibrator Ax2. The perforated vibration plate Ax1 is affixed to the piezoelectric vibrator Ax2 so as to cover an internal hole portion of the piezoelectric vibrator Ax2. Also, the perforated vibration plate Ax1 is attached such that the front surface thereof faces the inside of the room to be decontaminated and the rear surface faces the inside of the mist receiving container MRx, and a plurality of micropores of the perforated vibration plate Ax1 passes through the inside of the room to be decontaminated and the inside of the mist receiving container MRx. In FIGS. 5A, 5B, the perforated vibration plate Ax1 is disposed so as to discharge a hydrogen peroxide mist horizontally from the front surface of the perforated vibration plate Ax1, but the configuration is not restricted thereto, and it may be discharged downward or upward, depending on the position of the plate disposed.

In this state, the primary mist is discharged into the inside of the mist receiving container MRx through the primary mist supply pipe MLx. The rear surface of the perforated vibration plate Ax1 and an end of the primary mist supply pipe MLx are opposite each other inside the mist receiving container MRx. Accordingly, the discharged primary mist is ejected directly onto the rear surface of the perforated vibration plate Ax1 to be subjected to gas-liquid separation. The separated decontamination liquid is converted into a fine secondary mist (hydrogen peroxide mist) through a plurality of micropores of the perforated vibration plate Ax1 under ultrasonic vibration to be discharged into the inside of the room to be decontaminated and to provide decontamination effects. Even if part of the decontamination liquid subjected to gas-liquid separation on the rear surface of the perforated vibration plate Ax1 is retained in the liquid pool Mrx1, this is converted into a fine secondary mist, though in very small quantities, through a plurality of micropores of the perforated vibration plate Ax1 to be discharged into the inside of the room to be decontaminated. Meanwhile, the separated air is discharged from the air vent MRx2 into the outside.

Thus, since the amount of a decontamination liquid supplied to the ultrasonic atomizer Ax can accurately be controlled to the least possible amount, presence of residual decontamination liquid can be avoided for efficient decontamination even in cases where long pipes are installed for each of a plurality of rooms to be decontaminated. Moreover, since a precise amount of hydrogen peroxide mist can be thus supplied for each room, no shortage of decontamination liquid can occur and no failure is found on an ultrasonic vibrator, which is the core of the ultrasonic atomizer Ax. In addition, sufficient decontamination effects can be provided with the least possible amount of decontamination liquid to efficiently utilize a decontamination liquid.

Herein, the diameter and number of micropores of the perforated vibration plate Ax1 are not particularly restricted, and they may be determined so long as ultrasonic atomization effects and sufficient amount of a hydrogen peroxide mist can be provided. The diameter is normally 4 to 11 μm, but if it is less than a bacterial spore (e.g., 0.5 to about 3 μm or so), filtering effects are provided to cause no bacterial decontamination on a decontamination liquid.

Figure 6A:
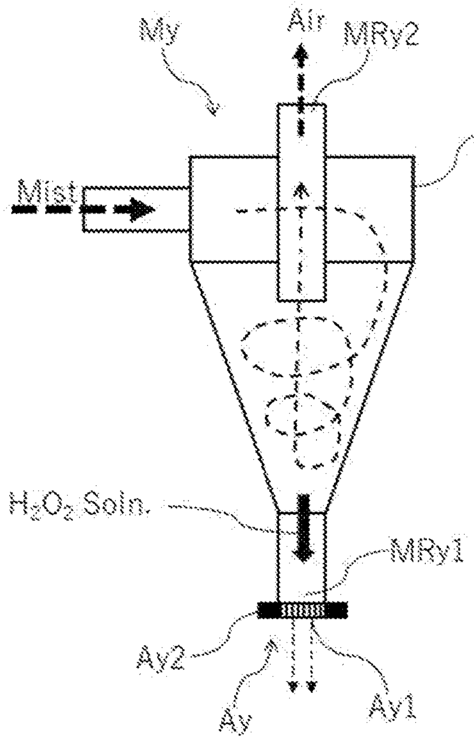
FIG. 6A is a schematic side cross-sectional view illustrating other exemplary secondary mist generation means used in the decontamination system of the present invention.
Figure 6B:
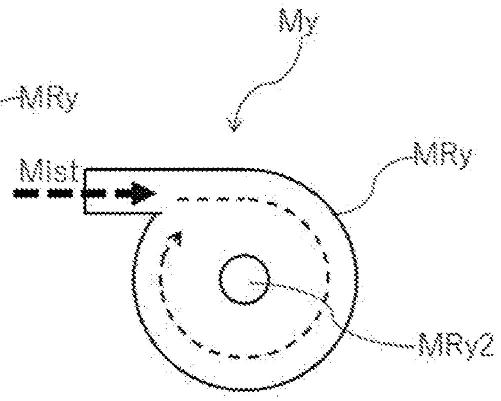
FIG. 6B is a schematic plan cross-sectional view illustrating the same.

Herein, other exemplary secondary mist generation means used in this first embodiment will be described. FIGS. 6A, 6B illustrates other exemplary secondary mist generation means. FIG. 6A is a schematic side cross-sectional view of other exemplary secondary mist generation means, and 6B is a schematic plan cross-sectional view thereof. In these figures, a hydrogen peroxide mist generation device My as a secondary mist generation means is shown composed of a mist receiving container MRy and an ultrasonic atomizer Ay.

The mist receiving container MRy is shaped to have a cyclone mechanism, and the ultrasonic atomizer Ay is attached to a lower end portion of the mist receiving container MRy. A lower end portion of an internal space to which the ultrasonic atomizer Ay is attached serves as a liquid pool MRy for a small amount of decontamination liquid subjected to gas-liquid separation. Also, an end of the primary mist supply pipe MLy radially communicates with an upper side surface of the mist receiving container MRy toward the inside of the mist receiving container MRy (corresponding to an inlet of the cyclone). The air vent MRy2 opens upward in the center of the upper end portion of the mist receiving container MRy.

The ultrasonic atomizer Ay is composed of a perforated vibration plate Ay1 formed of a substantially annular disk and provided with a plurality of micropores (not shown) atomizing the decontamination liquid (hydrogen peroxide solution) subjected to gas-liquid separation, the micropores passing through the perforated vibration plate between the front surface and the back surface thereof, a piezoelectric vibrator Ay2 formed of a substantially annular disk in which the perforated vibration plate Ay1 is subjected to film vibration, and a controller (not shown) controlling the vibration of the piezoelectric vibrator Ay2. The perforated vibration plate Ay1 is affixed to the piezoelectric vibrator Ay2 so as to cover an internal hole portion of the piezoelectric vibrator Ay2. Also, the perforated vibration plate Ay1 is attached such that the front surface thereof faces the inside of the room to be decontaminated and the rear surface faces the inside of the mist receiving container MRy, and a plurality of micropores of the perforated vibration plate Ay1 passes through the inside of the room to be decontaminated and the inside of the mist receiving container MRy. In FIGS.

6A, 6B, the perforated vibration plate Ay1 is disposed so as to discharge a hydrogen peroxide mist downward from the front surface of the perforated vibration plate Ay1, but the configuration is not restricted thereto, and it may be discharged horizontally, or upward, depending on the position of the plate disposed.

In this state, the primary mist is discharged into the inside of the mist receiving container MRy through the primary mist supply pipe MLy. The inside of the mist receiving container MRy, which is shaped to have a cyclone mechanism, allows the discharged primary mist to be subjected to gas-liquid separation on an internal side wall of the mist receiving container MRy. The separated decontamination liquid is collected in a liquid pool MRy1 of an internal lower end portion of the mist receiving container MRy, and converted into a fine secondary mist (hydrogen peroxide mist) through a plurality of micropores of the perforated vibration plate Ay1 under ultrasonic vibration to be discharged into the inside of the room to be decontaminated and to provide decontamination effects. Meanwhile, the separated air is discharged from the air vent MRy2 into the outside.

Thus, since the amount of a decontamination liquid supplied to the ultrasonic atomizer Ay can accurately be controlled to the least possible amount, presence of residual decontamination liquid can be avoided for efficient decontamination even in cases where long pipes are installed for each of a plurality of rooms to be decontaminated. Moreover, since a precise amount of hydrogen peroxide mist can be thus supplied for each room, no shortage of decontamination liquid can occur and no failure is found on an ultrasonic vibrator, which is the core of the ultrasonic atomizer Ay. In addition, sufficient decontamination effects can be provided with the least possible amount of decontamination liquid to efficiently utilize a decontamination liquid.

As obviously shown in the above first embodiment, the present invention can provide a decontamination system capable of efficiently using a decontamination liquid because large-scale equipment such as large-diameter ducts and anti-condensation heaters is not required, long pipes can be installed for each of a plurality of rooms to be decontaminated, a decontamination liquid is not present in supply pipes as a residual dead liquid, and a proper amount of decontamination liquid can essentially be supplied for each room to cause no fail me of an ultrasonic vibrator.

Second Embodiment

In this second embodiment, the case where the position of a hydrogen peroxide mist generation device is different from that in the first embodiment will be described. In FIG. 1 illustrating the above first embodiment, hydrogen peroxide mist generation devices M1 to Mn are disposed at an upper portion of HEPA filters H1 to Hn (adjacent to circulating fans F1 to Fn). On the contrary, FIG. 2 is a schematic block diagram illustrating the case where the position at which a secondary mist generation means is arranged in the above first embodiment is changed.

Figure 2:
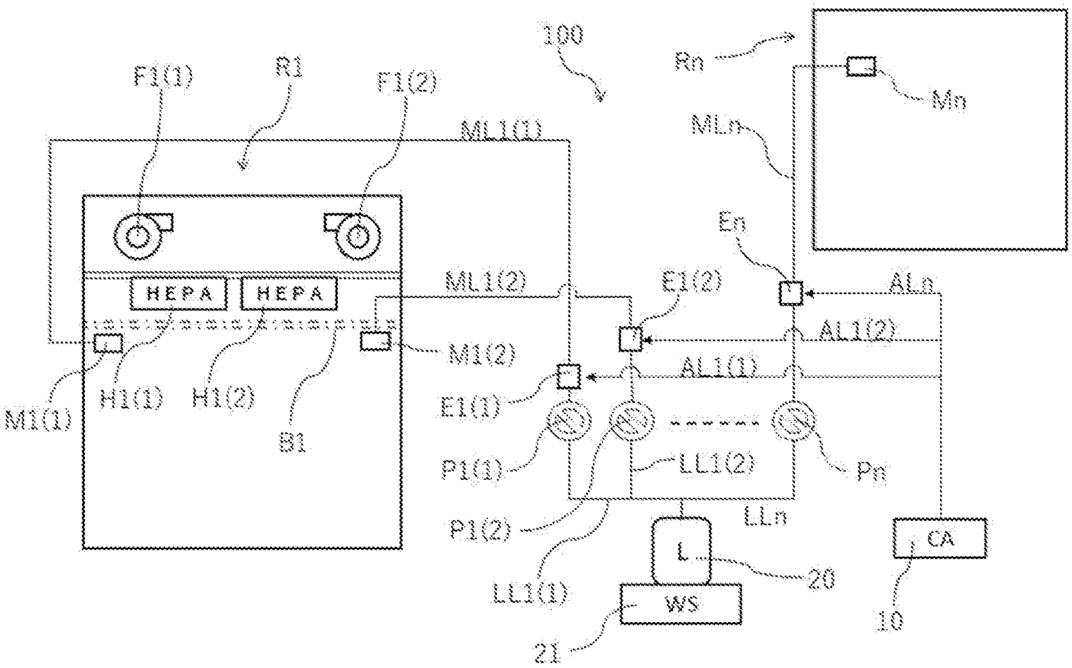
FIG. 2 is a schematic block diagram illustrating a second embodiment where the position at which a secondary mist generation means is arranged in the first embodiment illustrated in FIG. 1 is changed.

In FIG. 2 illustrating this second embodiment, the hydrogen peroxide mist generation devices M1 to Mn are disposed beneath straightening plates B1 to Bn above a work area. Specifically, in a room to be decontaminated R1, 2 hydrogen peroxide mist generation devices M1(1), M1(2) are disposed beneath the straightening plate B1 above the work area.

In FIG. 2, the position of the equipment other than the hydrogen peroxide mist generation devices M1 to Mn is the same as in FIG. 1. In this second embodiment, only the position of the hydrogen peroxide mist generation devices is different from that in the above first embodiment, and a mechanism of action and effects of the invention are the same as in the above first embodiment. Herein, repetitions of similar explanations are avoided.

Third Embodiment

Figure 3:
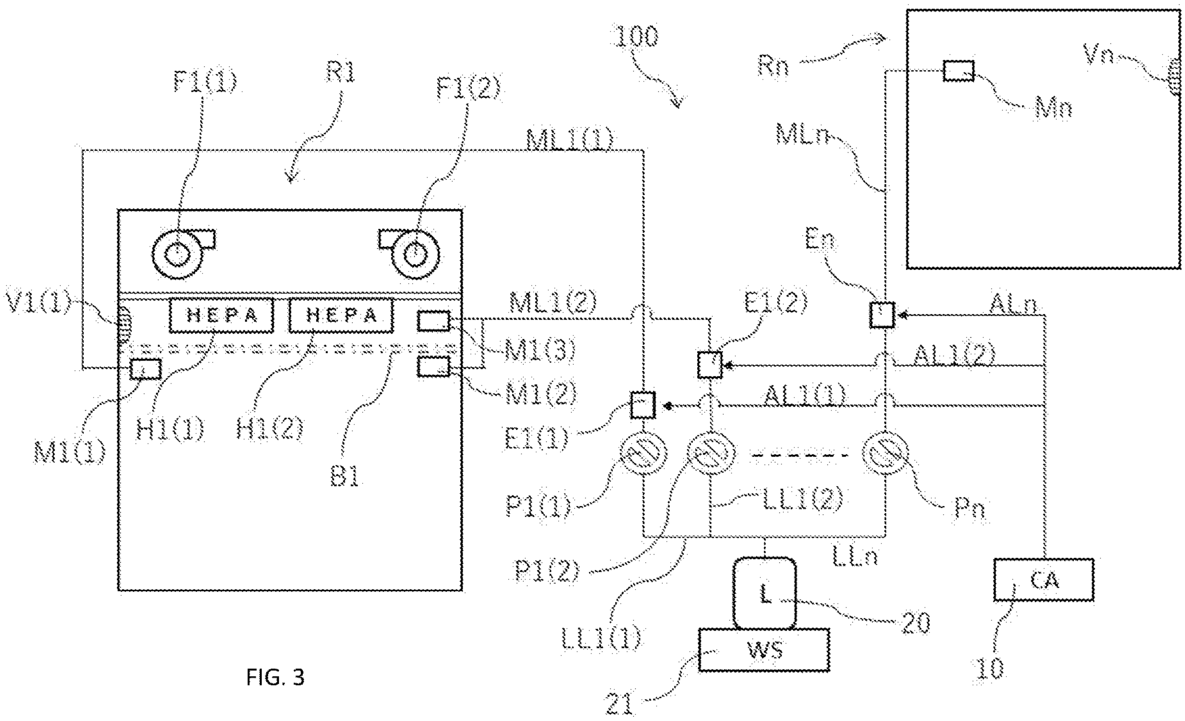
FIG. 3 is a schematic block diagram illustrating a third embodiment where the position at which the secondary mist generation means is arranged in the first embodiment in FIG. 1 is changed and a mist dispersion/diffusion device is disposed.

In this third embodiment, the case where the position of a hydrogen peroxide mist generation device is changed, and a mist dispersion/diffusion device for dispersing and diffusing a hydrogen peroxide mist is disposed will be described. FIG. 3 is a schematic block diagram where the position at which a secondary mist generation means is arranged in the above first embodiment is changed and a mist dispersion/diffusion device is disposed.

In FIG. 3 illustrating this third embodiment, hydrogen peroxide mist generation devices M1 to Mn are disposed beneath straightening plates B1 to Bn above a work area, as in the above second embodiment. Moreover, in FIG. 3, the hydrogen peroxide mist generation devices M1 to Mn and mist dispersion/diffusion devices V1 to Vn are disposed at an upper portion of the straightening plates B1 to Bn (between the straightening plates B1 to Bn and HEPA filters H1 to Hn, respectively). The mist dispersion/diffusion devices V1 to Vn each include an ultrasonic vibration plate.

Specifically, in a room to be decontaminated R1, 2 hydrogen peroxide mist generation devices M1(1), M1(2) are disposed beneath the straightening plate B1 above the work area. Moreover, one hydrogen peroxide mist generation device M1(3) and a mist dispersion/diffusion device V1(1) are disposed at an upper portion of the straightening plate B1 (between the straightening plate B1 and the HEPA filters H1(1) and H1(2)). In FIG. 3, the position of the equipment other than the hydrogen peroxide mist generation devices M1 to Mn and the mist dispersion/diffusion devices V1 to Vn is the same as in FIG. 1.

Herein, the mist dispersion/diffusion devices V1 to Vn will be described. In the room to be decontaminated R1 in FIG. 3, the mist dispersion/diffusion device V1(1) is disposed such that acoustic radiation pressure by ultrasonic vibration from the front in the discharge direction acts on a hydrogen peroxide mist discharged leftward in the figure horizontally from the hydrogen peroxide mist generation device M1(3).

Herein, the structure and operation of one exemplary mist dispersion/diffusion device V1(1) will be described. The mist dispersion/diffusion device V1(1) includes an ultrasonic vibration plate composed of a base and a plurality of transmitters. In this third embodiment, the transmitter used is an ultrasonic transmitter. In this third embodiment, a plurality of ultrasonic transmitters is arranged on the base so as to be uniform in transmission direction of a vibrating surface or dispersed in multiple directions. The number of ultrasonic transmitters is not particularly restricted.

In this third embodiment, an ultrasonic transmitter of frequency modulation system for transmitting an ultrasound whose frequency is around 40 KHz is used. The type, size, structure and output of the ultrasonic transmitter are not particularly restricted. In this third embodiment, the ultrasonic vibration plate is not restricted to an ultrasonic transmitter, and the ultrasonic generation mechanism, frequency range and output are not particularly restricted.

In this third embodiment, a controller controls the frequency, output, and transmission time of an ultrasonic transmitter, and the pressure on the hydrogen peroxide mist by acoustic radiation pressure can be changed in stationary operation, intermittent operation or stronger/weaker operation of ultrasonic transmission.

In this configuration, a hydrogen peroxide mist (secondary mist) discharged from the hydrogen peroxide mist generation device M1(3) is uniformly dispersed and diffused in a space between the straightening plate B1, and the HEPA filter H1(1) and H1(2) by operating the mist dispersion/diffusion device V1(1). In addition, a hydrogen peroxide mist is further refined by acoustic radiation pressure to assuredly decontaminate the space between the straightening plate B1, and the HEPA filter H1(1) and H1(2), and the HEPA filters.

In this third embodiment, since the hydrogen peroxide mist is further refined by ultrasonic vibration to have smaller particle sizes and larger surface areas, it is believed that the evaporation efficiency of mists is high, resulting in repeated evaporation and condensation. The hydrogen peroxide mist is a highly-refined mist to form a uniform and thin condensed film on an internal wall surface of the room to be decontaminated R1. Accordingly, it is believed that ultrafine particles of hydrogen peroxide 3 μm or less and a hydrogen peroxide gas are subjected to phase change for coexistence inside the room to be decontaminated R1 to provide a high-level decontamination environment.

Fourth Embodiment

Figure 4:
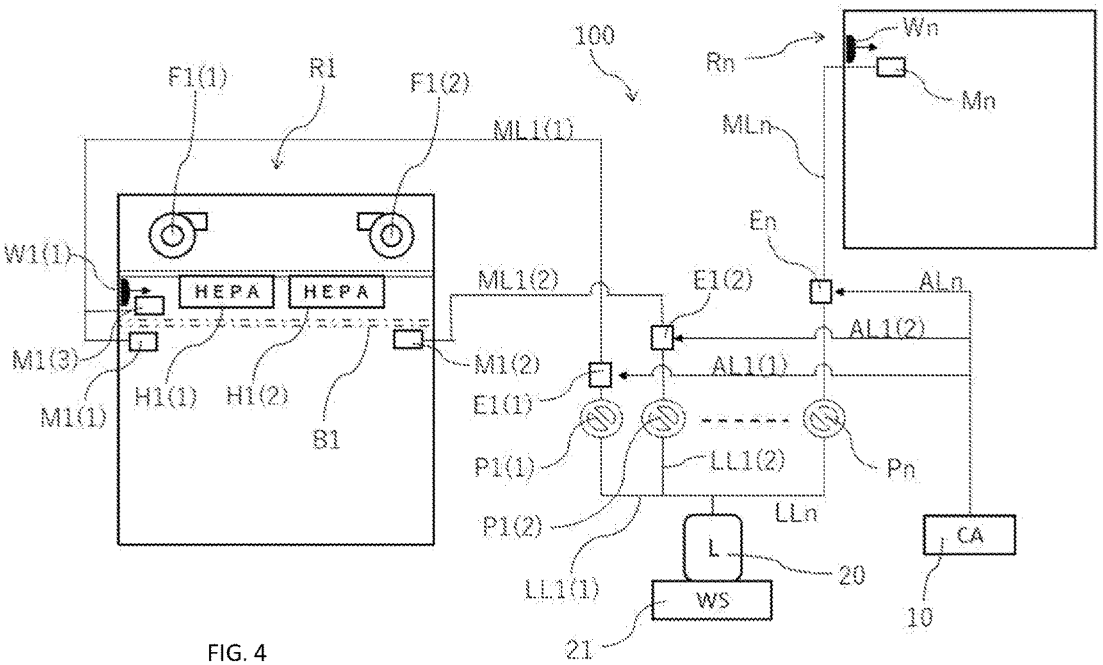
FIG. 4 is a schematic block diagram illustrating a fourth embodiment where the position at which the secondary mist generation means is arranged in the first embodiment in FIG. 1 is changed and a mist diffusion device is disposed.

In this fourth embodiment, the case where the position of a hydrogen peroxide mist generation device is changed, and a mist diffusion device for dispersing and diffusing a hydrogen peroxide mist is disposed will be described. FIG. 4 is a schematic block diagram illustrating a fourth embodiment where the position at which a secondary mist generation means is arranged in the above first embodiment is changed and a mist diffusion device is disposed.

In FIG. 4 illustrating this fourth embodiment, hydrogen peroxide mist generation devices M1 to Mn are disposed beneath straightening plates B1 to Bn above a work area, as in the above second embodiment. Moreover, in FIG. 4, the hydrogen peroxide mist generation devices M1 to Mn and mist diffusion devices W1 to Wn are disposed at an upper portion of the straightening plates B1 to Bn (between the straightening plates B1 to Bn and HEPA filters H1 to Hn, respectively). The mist diffusion devices W1 to Wn each include an axial fan, and disposed adjacent to the hydrogen peroxide mist generation devices M1 to Mn.

Specifically, in a room to be decontaminated R1, 2 hydrogen peroxide mist generation devices M1(1), M1(2) are disposed beneath the straightening plate B1 above the work area. Moreover, one hydrogen peroxide mist generation device M1(3) and a mist diffusion device W1(1) are disposed at an upper portion of the straightening plate B1 (between the straightening plate B1, and the HEPA filters H1(1) and H1(2)) adjacent to the hydrogen peroxide mist generation device M1(3). In FIG. 4, the position of the equipment other than the hydrogen peroxide mist generation devices M1 to Mn and the mist dispersion/diffusion devices W1 to Wn is the same as in FIG. 1.

Herein, the mist diffusion devices W1 to Wn will be described. In the room to be decontaminated R1 in FIG. 4, the mist diffusion device W1(1) is disposed such that the pressure by air flow substantially parallel to the discharge direction acts on a hydrogen peroxide mist discharged rightward in the figure horizontally from the hydrogen peroxide mist generation device M1(3).

Also, the mist diffusion device W1(1) may be installed such that its air flow discharge direction slants to a hydrogen peroxide mist discharged rightward in the figure horizontally from the hydrogen peroxide mist generation device M1(3). The air flow discharge direction slants to the hydrogen peroxide mist discharge direction, preferably at 0° to 45°, more preferably 5° to 30°. Moreover, when the mist diffusion device W1(1) used is a fan for generating spiral air flow such as axial fan, it is preferably disposed such that a hydrogen peroxide mist discharged from the mist generation device M1(3) is pressed with the spiral air flow rotation tangential direction upward.

Herein, the mist diffusion device W1(1) is preferably an ordinary axial fan, and it can be a Sirocco fan. Also, a nozzle discharging compressed air or the like may be used, and it is not particularly restricted so long as it is a method for generating air flow to diffuse as far as possible a mist generated from a hydrogen peroxide mist generation device even in a narrow space between a straightening plate B1, and HEPA filters H1(1) and H1(2).

In this fourth embodiment, a controller controls the output and operation time of an axial fan, and the pressure on the hydrogen peroxide mist by air flow can be changed in stationary operation, intermittent operation or stronger/weaker operation of the axial fan.

In this configuration, a hydrogen peroxide mist (secondary mist) discharged from the hydrogen peroxide mist generation device M1(3) is uniformly diffused in a space between the straightening plate B1, and the HEPA filters H1(1) and H1(2) by operating the mist diffusion device W1(1) to assuredly decontaminate the space between the straightening plate B1, and HEPA filters H1(1) and H1(2) and the HEPA filters.

As obviously shown in the above second to fourth embodiments, the present invention can provide a decontamination system capable of efficiently using a decontamination liquid because large-scale equipment such as large-diameter ducts and anti-condensation heaters is not required, long pipes can be installed for each of a plurality of rooms to be decontaminated, a decontamination liquid is not present in supply pipes as a residual dead liquid, and a proper amount of decontamination liquid can essentially be supplied for each room to cause no failure of an ultrasonic vibrator.

The present invention is achieved not only by each of the above embodiments, but also by the following various alternatives.

(1) In each of the above embodiments, the compressed air generation means employed is an air compressor, but the means is not restricted thereto, and other means such as a high pressure air cylinder may be used.

(2) In each of the above embodiments, the primary mist generation means employed is an ejector, but the means is not restricted thereto, and other gas-liquid mixing means such as a gas-liquid pump may be used.

(3) In each of the above embodiments, a tube pump is employed for a conduit line of a decontamination liquid supply pipe, but the tube pump is not restricted thereto, and any other pump or liquid supply means may be used.

(4) In the above third embodiment, a mist dispersion/diffusion device (ultrasonic vibration plate) for dispersing and diffusing a hydrogen peroxide mist is disposed at an upper portion of a straightening plate (between the straightening plate, and HEPA filters H1 to Hn), but the arrangement is not restricted thereto, and it may be arranged beneath a straightening plate above a work area or at any position in the work area.

(5) In the above fourth embodiment, a mist diffusion device (axial fan) for dispersing and diffusing a hydrogen peroxide mist is disposed at an upper portion of a straightening plate (between the straightening plate, and HEPA filters H1 to Hn), but the arrangement is not restricted thereto, and it may be arranged beneath a straightening plate above a work area or at any position in the work area.

REFERENCE SIGNS LIST

100 . . . Decontamination system, 10 . . . Air compressor, AL1 to ALn . . . Air supply pipe,

20 . . . Hydrogen peroxide solution tank, 21 . . . Weighing device, LL1 to LLn . . . Decontamination liquid supply pipe, P1 to Pn . . . Tube pump, E1 to En . . . Ejector, ML1 to MLn, MLx, MLy . . . Primary mist supply pipe, M1 to Mn, Mx, My . . . Hydrogen peroxide mist generation device, MR1 to MRn, MRx, MRy . . . Mist receiving container, MRx1, MRy1 . . . Liquid pool, MRx2, MRy2 . . . Air vent, MRx3 . . . Baffle plate, A1 to An, Ax, Ay . . . Ultrasonic atomizer, Ax1, Ay1 . . . Perforated vibration plate, Ax1, Ay2 . . . Piezoelectric vibrator, V1 to Vn . . . Ultrasonic vibration plate, W1 to Wn . . . Axial fan, R1 to Rn . . . Room to be decontaminated, F1 to Fn . . . Circulating fan, H1 to Hn . . . HEPA filter, MH . . . Hydrogen peroxide decomposition filter, B1 to Bn . . . Straightening plate.

What is claimed is:

1. A decontamination system for decontaminating the inside of at least one room to be decontaminated using a mist for decontamination, the system comprising:

a compressed air generation means configured to generate compressed air and a decontamination liquid supply means configured to supply a decontamination liquid that constitutes a mist for decontamination, primary mist generation means configured to generate a primary mist by mixing the compressed air and the decontamination liquid for the at least one room to be decontaminated, at least one secondary mist generation means configured to convert the decontamination liquid subjected to gas-liquid separation from the primary mist into a fine secondary mist, air supply pipes configured to establish operable communication from the compressed air generation means to the primary mist generation means, decontamination liquid supply pipes configured to establish operable communication from the decontamination liquid supply means to the primary mist generation means, and primary mist supply pipes configured to establish operable communication from the primary mist generation means to the at least one secondary mist generation means, wherein:

the at least one secondary mist generation means comprises primary mist receiving containers and ultrasonic atomizers, each of the primary mist receiving containers comprises an air vent configured to discharge the air subjected to gas-liquid separation from the primary mist supplied through the primary mist supply pipes to the outside, and each of the ultrasonic atomizers comprises a piezoelectric vibrator and a perforated vibration plate provided with a plurality of micropores dimensioned to atomize the decontamination liquid subjected to gas-liquid separation by vibration of the piezoelectric vibrator, the micropores passing through the perforated vibration plate between a front surface thereof and a back surface thereof.

2. The decontamination system according to claim 1, wherein:

the compressed air generation means, the decontamination liquid supply means, and each of the primary mist generation means are arranged so as to be separate from the at least one room to be decontaminated through the primary mist supply pipes, each of the at least one secondary mist generation means is arranged adjacent to a corresponding of the at least one room to be decontaminated or indoor through each of the primary mist supply pipes, whereby a conveyance distance of each of the primary mist supply pipes to the at least one room to be decontaminated is longer than a conveyance distance of each of the decontamination liquid supply pipes corresponding to the at least one room to be decontaminated.

3. The decontamination system according to claim 2, wherein:

the ultrasonic atomizer is disposed such that the front surface of the perforated vibration plate faces the inside of the at least one room to be decontaminated and the rear surface thereof faces an inside of the primary mist receiving container, and the primary mist supplied to the primary mist receiving container is ejected from the primary mist supply pipe onto the rear surface of the perforated vibration plate to be subjected to gas-liquid separation, and is atomized when the separated decontamination liquid moves from the rear surface of the perforated vibration plate to the front surface of the perforated vibration plate to be discharged from the front surface into the inside of the at least one room to be decontaminated.

4. The decontamination system according to claim 2, wherein:

the ultrasonic atomizer is disposed such that the front surface of the perforated vibration plate faces the inside of the at least one room to be decontaminated and the rear surface thereof faces a liquid pool provided at an internal lower end portion of the primary mist receiving container, and the primary mist supplied to the primary mist receiving container is discharged from the primary mist supply pipe into the inside of the primary mist receiving container to be subjected to gas-liquid separation, and is atomized after the separated decontamination liquid is collected at the liquid pool of the primary mist receiving container and moves from the rear surface of the perforated vibration plate to the front surface of the perforated vibration plate to be discharged from the front surface into the inside of the at least one room to be decontaminated.

5. The decontamination system according to claim 4, wherein:

the primary mist receiving container is spindle-shaped or semi-spindle-shaped with a focusing lower end portion, or has a spindle-shaped cross section or a semi-spindle-shaped cross section with a focusing lower end portion, and the supplied primary mist is subjected to gas-liquid separation, the separated decontamination liquid is collected at the liquid pool provided at the lower end portion and the separated air is discharged from the air vent provided at an upper end portion into an outside.

6. The decontamination system according to claim 4, wherein:

the primary mist receiving container is configured to subject the primary mist supplied by a cyclone mechanism to gas-liquid separation, a separated decontamination liquid is collected at the liquid pool provided at the lower end portion and the separated air is discharged from the air vent provided at the upper end portion into the outside.

7. The decontamination system according to claim 2, comprising mist dispersion/diffusion means configured to disperse and diffuse the secondary mist, wherein:

each of the mist dispersion/diffusion means comprises an ultrasonic vibration plate disposed on an internal wall surface of the at least one room to be decontaminated, the ultrasonic vibration plate is subjected to ultrasonic vibration by ultrasound to generate sound flows from a plate surface, and the secondary mist discharged from the at least one secondary mist generation means is pressed by acoustic radiation pressure in stationary operation, intermittent operation, or stronger/weaker operation to disperse and diffuse the secondary mist.

8. The decontamination system according to claim 7, configured to further refine the secondary mist supplied to the inside of the decontamination region by ultrasonic vibration generated from the ultrasonic vibration plate.

9. The decontamination system according to claim 2, comprising the at least one mist diffusion means configured to disperse and diffuse the secondary mist, wherein:

each of the at least one mist diffusion means includes an axial fan disposed adjacent to the at least one secondary mist generation means, the secondary mist discharged from the at least one secondary mist generation means by the axial fan is pressed by air flow in stationary operation, intermittent operation, or stronger/weaker operation to disperse and diffuse the secondary mist.

10. The decontamination system according to claim 1, wherein:

the ultrasonic atomizer is disposed such that the front surface of the perforated vibration plate faces the inside of the at least one room to be decontaminated and the rear surface thereof faces an inside of the primary mist receiving container, and the primary mist supplied to the primary mist receiving container is ejected from the primary mist supply pipe onto the rear surface of the perforated vibration plate to be subjected to gas-liquid separation, and is atomized when the separated decontamination liquid moves from the rear surface of the perforated vibration plate to the front surface of the perforated vibration plate to be discharged from the front surface into the inside of the at least one room to be decontaminated.

11. The decontamination system according to claim 1, wherein:

the ultrasonic atomizer is disposed such that the front surface of the perforated vibration plate faces the inside of the at least one room to be decontaminated and the rear surface thereof faces a liquid pool provided at an internal lower end portion of the primary mist receiving container, and the primary mist supplied to the primary mist receiving container is discharged from the primary mist supply pipe into the inside of the primary mist receiving container to be subjected to gas-liquid separation, and is atomized after the separated decontamination liquid is collected at the liquid pool of the primary mist receiving container and moves from the rear surface of the perforated vibration plate to the front surface of the perforated vibration plate to be discharged from the front surface into the inside of the at least one room to be decontaminated.

12. The decontamination system according to claim 11, wherein:

the primary mist receiving container is spindle-shaped or semi-spindle-shaped with a focusing lower end portion, or has a spindle-shaped cross section or a semi-spindle-shaped cross section with a focusing lower end portion, and the supplied primary mist is subjected to gas-liquid separation, the separated decontamination liquid is collected at the liquid pool provided at the lower end portion and the separated air is discharged from the air vent provided at an upper end portion into an outside.

13. The decontamination system according to claim 11, wherein:

the primary mist receiving container is configured to subject the primary mist supplied by a cyclone mechanism to gas-liquid separation, a separated decontamination liquid is collected at the liquid pool provided at the lower end portion and the separated air is discharged from the air vent provided at the upper end portion into the outside.

14. The decontamination system according to claim 1, comprising mist dispersion/diffusion means configured to disperse and diffuse the secondary mist, wherein:

each of the mist dispersion/diffusion means comprises an ultrasonic vibration plate disposed on an internal wall surface of the at least one room to be decontaminated, the ultrasonic vibration plate is subjected to ultrasonic vibration by ultrasound to generate sound flows from a plate surface, and the secondary mist discharged from the at least one secondary mist generation means is pressed by acoustic radiation pressure in stationary operation, intermittent operation, or stronger/weaker operation to disperse and diffuse the secondary mist.

15. The decontamination system according to claim 14, configured to further refine the secondary mist supplied to the inside of the decontamination region by ultrasonic vibration generated from the ultrasonic vibration plate.

16. The decontamination system according to claim 1, comprising at least one mist diffusion means configured to disperse and diffuse the secondary mist, wherein:

each of the at least one mist diffusion means includes an axial fan disposed adjacent to the at least one secondary mist generation means, the secondary mist discharged from the at least one secondary mist generation means by the axial fan is pressed by air flow in stationary operation, intermittent operation, or stronger/weaker operation to disperse and diffuse the secondary mist.

* * * * *